United States Patent [19]

Martin

[11] 4,313,437
[45] Feb. 2, 1982

[54] TRACHEOTOMY AND ENDOTRACHEAL TUBE RETAINERS

[76] Inventor: Dianne L. Martin, 3903 Barrington, Apt. 301, San Antonio, Tex. 78217

[21] Appl. No.: 80,982

[22] Filed: Oct. 1, 1979

[51] Int. Cl.³ .......................................... A61M 25/02
[52] U.S. Cl. ....................... 128/207.17; 128/DIG. 15
[58] Field of Search ....................... 128/207.17, 207.14, 128/DIG. 15, 134, 207.15, DIG. 26, 200.26, 207.11, 206.17, 207.18, 201.11, 206.12, 206.18, 206.19, 207.13

[56] References Cited

U.S. PATENT DOCUMENTS

| | | | |
|---|---|---|---|
| 1,317,947 | 10/1919 | Sodenling | 128/206.17 |
| 2,400,077 | 5/1946 | Dauster | 128/207.11 |
| 2,928,387 | 3/1960 | Layne | 128/207.11 |
| 3,086,529 | 4/1963 | Munz et al. | 128/DIG. 15 |
| 3,568,670 | 3/1971 | Gaylord, Jr. | 128/DIG. 15 |
| 3,586,001 | 6/1971 | Sanderson | 128/DIG. 15 |
| 3,688,774 | 9/1972 | Ahiyania | 128/207.17 |
| 3,774,616 | 11/1973 | White et al. | 128/207.14 |
| 3,903,878 | 9/1975 | Spann | 128/77 |
| 3,946,742 | 3/1976 | Eross | 128/207.14 |
| 3,972,321 | 8/1976 | Proctor | 128/DIG. 26 |
| 4,027,666 | 6/1977 | Marx | 128/DIG. 15 |

Primary Examiner—Henry J. Recla
Attorney, Agent, or Firm—Gunn, Lee & Jackson

[57] ABSTRACT

A retainer encircling the neck of a patient and retaining a tracheotomy or endotracheal tube in position on the patient. An elongated, elastic, foam-filled body is designed to project around the nape of the neck of the patient. An elongated tape tab extends from each end of the foam-filled body and includes hook means, such as Velcro, securely attached adjacent the end of each tape. The tapes are designed to project through the slots in tracheotomy or endotracheal tube base permitting the tapes to be folded back over a portion of the fabric covering of the elastic, foam-filled body in contact and secure to the body for attaching the tracheotomy or endotracheal tube in the desired position. The elastic body is covered with a stretch, knit fabric having a flannel-like outer surface which is particularly adaptable to contact and engage Velcro tabs. Some of the principal advantages of the device of this invention are ease of securing the device around the neck of the patient with a one-handed operation and the soft, elastic foam-filled body is comfortable to skin contact and does not rub or chafe the skin. The elastic characteristic permits expansion to compensate for swelling or contraction of the neck of the patient. The device facilitates in maintaining the sterile environment on and around tracheotomy, endotracheal, and intubation tubes.

7 Claims, 6 Drawing Figures

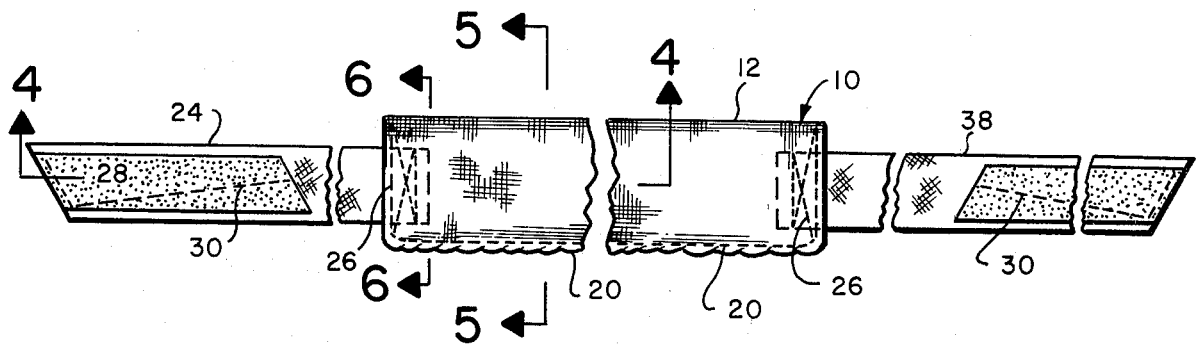
FIG. 3
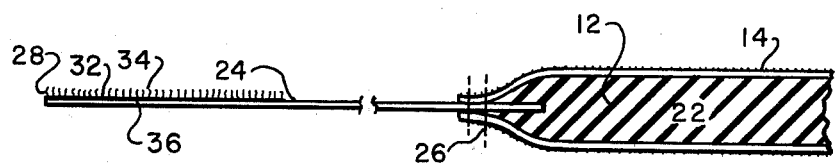
FIG. 4
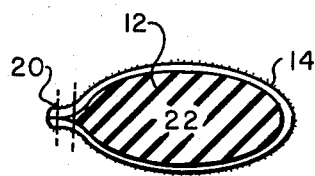    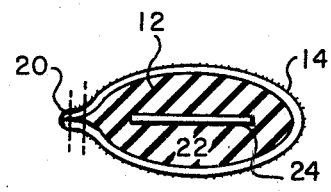
FIG. 5                          FIG. 6

TRACHEOTOMY AND ENDOTRACHEAL TUBE RETAINERS

BACKGROUND OF THE INVENTION

One area of hospital care requiring substantial hours of skilled nursing time is encountered in nursing of severely injured or ill patients requiring tracehotomy or endotracheal tubes. Adjustment or replacement of the retention means around the neck of the patient is frequently required at approximately eight-hour intervals. The most common methods used for retaining tracehotomy or endotracheal tube bases in position is by utilization of adhesive tape or the tying of umbilical tape to the tube base and around the patient's neck. This care must be accomplished in a sterile environment and extreme caution exercised to avoid unintentional displacement of means utilized for ventilating the patient.

FIELD OF THE INVENTION

The device of this invention pertains to a strap or retainer with moderate elasticity cushioned surface for contacting the skin of the patient's neck. The fastening means providing an infinite degree of adjustment requires no buckling buttoning, snapping, or tying.

DESCRIPTION OF THE PRIOR ART

One of the more generally accepted writings pertaining to the area of use of this invention is the book *Respiratory Intensive Care in Nursing* by Sharon Bushnell, R.N. The work alludes to problems and difficulties encountered, the degree of intensive care required, and procedures followed in maintaining the aseptic environment while giving proper care during tracheotomy and/or using endotracheal tubes and intubation tubes. In an effort to facilitate and simplify the latest nursing procedures, various devices have been developed, some of which have been patented, such as U.S. Pat. No. 3,688,774 to Tachiro and Ahiyama. The Ahiyama device utilized an adjustable belt 32 fitting around the neck of the patient. Another invention is the U.S. Pat. No. 3,774,616, to White, utilizing a strap 22 with a series of holes 23 which attach to anchor pin 21. Another approach to the solution of the problem is U.S. Pat. No. 3,946,742, to Eruss, comprising endotracheal tube holder fastener 16 with a neck strap 14 having apertures 18 attaching to fastener 16. The device of this invention was conceived and developed to overcome various limitations of existing devices to simplify and assist in intensive nursing care. One of the purposes of this invention was to provide a comfortable retainer not irritating or chafing the skin of the patient. Another object was to provide infinite degrees of adjustment. Another object was to provide a soft, cushioned retainer with a sufficient degree of elasticity to compensate for slight swelling of the neck or expansion of the neck in the act of coughing. Further advantages will be apparent from presentation in the drawings, description of the construction of the device, and its operation and utilization.

SUMMARY OF THE INVENTION

The device of this invention is constructed in various sizes to provide for comfortable utilization by children as well as adults. The device, in summary, is a retainer encircling the neck of a patient having tape tabs extending from elastic foam filled body with means for securing the tape through the slots in the tracheotomy or endotracheal tube base with the ends of the tape folding back over the elastic foam filled body attaching to the body and retaining the tracheotomy and endotracheal tube firmly in position. The foam filled body of this device is constructed from stretch knit fabric having a flannel-like surface encasing elastic foam rubber filler with the foam filled body substantially encircling the neck of the patient. Other hook or securing means might be utilized for attaching the first and second attaching tapes to the foam filled body. When they are projected through the slot and folded back over the body, the preferred means for securing is by utilization of a Velcro tab secured to each end of the tape with the Velcro tabs including Velcro hooks which attach to the flannel surface of the foam filled body. This method is preferred in that it provides a simple, one-handed means for attaching with infinite degree of adjustment. Velcro hooks will secure satisfactorily to the flannel surface even in the presence of blood, oils, creams, and other fluids.

BRIEF DESCRIPTION OF THE DRAWINGS

For a more detailed description of the construction and utilization of the device, reference is made to the following drawings and subsequent detailed description of the preferred embodiment which will utilize identical reference characters to refer to identical or equivalent components throughout the various view and the following detailed description.

FIG. 3 is a plan view of the tracheotomy and endotracheal tube retainer partially fragmented to permit a foreshortening and more detailed pictorial illustration.

FIG. 4 is a sectional view of FIG. 2 fragmented and taken substantially along line 4—4 of FIG. 3 as viewed in the direction of the arrows.

FIG. 5 is a sectional view through FIG. 3 taken substantially on line 5—5 looking in the direction of the arrows, illustrating stretch-knit fabric, flannel surface, and the foam filled body.

FIG. 6 is a sectional view of FIG. 3 taken substantially on the lines of 6—6 looking in the direction of the arrow, depicting in a measure the method of securing the attaching tape to the foam filled body.

DESCRIPTION OF THE PREFERRED EMBODIMENT

Figure 1:
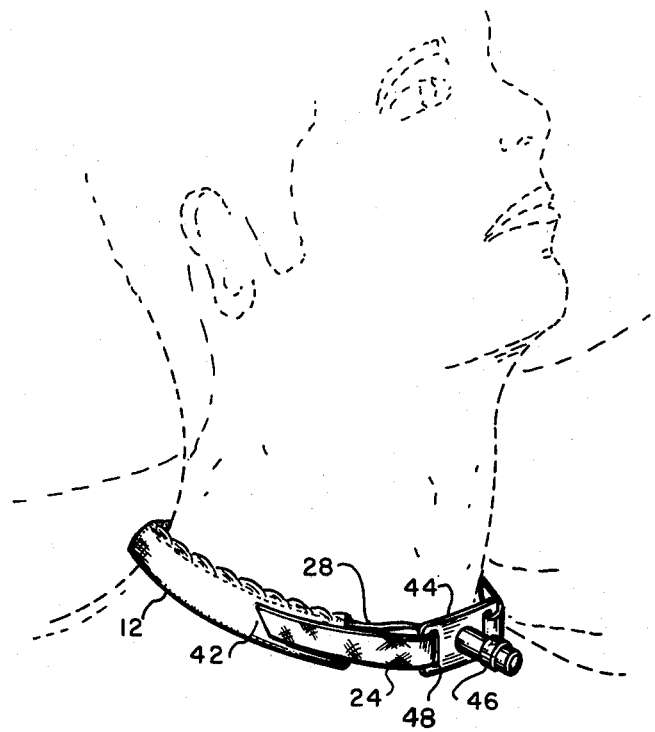
FIG. 1 is a perspective view illustrating the device simulating a tracheotomy tube secured to a tube base and retained by tracheotomy collar on a simulated patient.

For an illustration of the detail of the construction of the preferred embodiment, reference is particularly made to FIGS. 3-6. Tracheotomy and endotracheal tube retainer 10 are preferably constructed in various sizes to accomodate variation in size of the patient. For utilization on infants and children, small size having a length adequate to accomodate the neck size of six to eleven inches is desirable. For utilization on most adult females, the length to fit the neck size of ten to fifteen inches is desirable. Large sizes for primarily men should accomodate a neck size of fourteen to nineteen inches. Medium size structure of this device would have an overall length of about twenty-one inches. The foam filled body portion 12 would be approximately eight inches in length. This is constructed utilizing a stretch knit fabric 14 having an outer flannel-like surface. The interior of the material would be a stretch knit inner surface 18. The stretch knit fabric 14 is secured by a cross-stitch enclosure 20 encasing elastic foam rubber filler 22. A zig-zag cross-stitch enclosure 20 is utilized having a slight projection of the elastic foam rubber filler between each stitch to insure the desired elasticity or stretchability in the foam filled body 12 portion. The overall construction is illustrated in FIG. 3 and FIG. 4.

The first attaching tape 24 is secured to the first end of foam filled body 12. This tape 24 is preferably secured by tape stitching 26 which encloses the first end of the foam filled body 12. Other means for attaching the loose ends of the tape as they fold back over the foam filled body 12 may be employed; however, the preferable method developed is the utilization of Velcro tab 28 attached to the tape by Velcro stitching 30 which projects through Velcro base panels 32 and the first attaching tape 24. The Velcro tabs 28 have Velcro hooks 34 projecting up from the Velcro base panel which may be additionally secured to the first attaching tape by a Velcro base adhesive 36. To complete the construction of the device of this invention, the second attaching tape 38 is secured to the second end of the foam filled body 12. For an illustration of the utilization of the devices of this invention in a tracheotomy situation, reference is made to FIG. 1. Tracheotomy collar 42 encircles the neck of the patient with the foam filled body 12 projecting around the back of the neck of the patient. The device will retain the tracheotomy tube base 44 in position holding the tracheotomy tube 46 in the trachea of the patient. The first attaching tape 24 projects through retention slot 48 and would fold back with the Velcro tabs 28 contacting the flannel surface 16 of the foam filled body securing the first attaching tape 24 in position.

Figure 2:
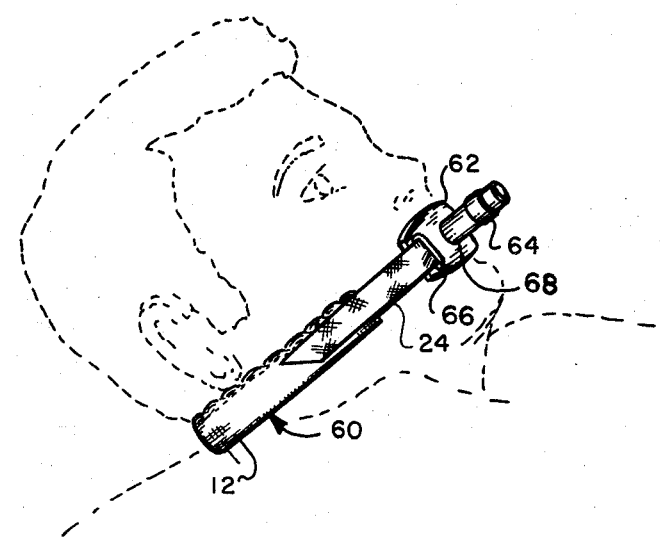
FIG. 2 is a related view illustrating an endotracheal tube secured to a base simulating retention in the mouth of the patient by an endotracheal tube collar.

To illustrate the utilization of the device of this invention in an endotracheal tube collar 60 configuration, reference is particularly made to FIG. 2. Endotracheal tube base 62 is positioned on the patient as illustrated in FIG. 2 with the endotracheal tube 64 projecting into the trachea of the patient. In a similar fashion as just previously described, the first attaching tape 24 would project through retention slot 66 with the first attaching tape 24 projecting through retention slot 66 and the Velcro tab 28 folds over and contacts the flannel surface 16 of the foam filled body 12 retaining the device in position.

OPERATION AND UTILIZATION OF THE DEVICE

The operation and utilization of the device of this invention has, in a measure, previously been described, particularly in reference to the illustration of FIG. 1 and FIG. 2. In the performance of the necessary duties in respiratory intensive care nursing in single canular care of tracheotomies, all gauze, equipment, canulars, intubation tubes, sponges, and tapes must be aseptic. The nurse performs the care with surgically sterile rubber gloves. Sterile water, hydrogen peroxide, antibiotic ointments, such as bacitracin, are utilized. In placing and adjusting the canular into position following the old methods employing tape, the tape was normally secured by a knot at the side of the neck. This procedure is quite important. If the tape is too loose, the canular will slide up and down in the trachea causing stenosis of the tissue in the area. If the tape is too tight, it causes discomfort to the patient and may compress the external jugular vein. In this routine procedure, which is accomplished either every eight hours or more often if necessary, the merits of the device of this invention are apparent. The attaching tapes 24 and 38, which are secured by Velcro tabs 28 to the flannel surface 16 of the foam filled body 12, permit infinite degrees of adjustment by mere repositioning of the Velcro tabs 28 on the foam filled body 12. This avoids the arduous task of tying a knot in a particular desired position. In addition to saving the valuable time of a skilled nurse, the device of this invention adds to the comfort of the patient, insures against the too loose or too tight retention of the canular intubation tube in position, guards against stenosis or other related injuries to the trachea of the patient. In addition to the comfort factor provided by the foam filled body 12 with the elastic characteristics of stretch knit fabric 14 and the elastic foam rubber filler 22, the elasticity of the retainer 10 makes allowances for the swelling of the neck of the patient or distention of the neck during the act of coughing. The characteristic of the device of this invention also when properly, snugly adjusted into position will compensate for an abatement of swelling in the neck of the patient.

The device of this invention has been described in its utilization in two particular interrelated configurations of tracheotomy and endotracheal tube. The device is susceptible of utilization in any nursing environment requiring retention of canulars or intubation tubes in the nose, mouth, or throat of a patient.

Having described in detail the construction and utilization of the device in its most frequently utilized environment, what is desired to be claimed is all utilizations or modifications of this device not departing from the scope of equivalents of the invention as defined in the appended claims.

I claim:

1. An intubation tube retainer to be used in conjunction with a tracheotomy or endotracheal tube holder having slots in either end thereof to secure a tracheotomy or endotracheal tube to a patient, said retainer comprising:
   a. an elongated, elastic body having a first end and a second end;
   b. a first attaching tape secured to the first end of said body;
   c. a second attaching tape secured to the second end of said body;
   d. securing means attached to at least one of said attaching tapes, said attaching tapes adapted to releasably secure said tracheotomy or endotracheal tube holder via said slots in position on said patient; and
   e. said elastic body further comprising an outer covering of stretch knit fabric, an elastic filler encased in said stretch knit fabric, and an expandable stitch securing an edge of said stretch knit fabric.

2. The invention of claim 1 comprising a multiplicity of securing means at least one attached to said first tape and at least one attached to said second tape.

3. The invention of claim 1 wherein said securing means are hooks connecting to said stretch knit fabric.

4. The invention of claim 1 wherein said securing means is Velcro fabric for hooking to said stretch knit fabric.

5. The invention of claim 1 wherein said securing means are adjacent the end of each of said attaching tapes.

6. An endotracheal or tracheotomy tube retainer to be used in conjunction with a tracheotomy or endotracheal tube holder having holes in ends thereof for holding an endotracheal or tracheotomy tube in position on a patient comprising:
   a. an elongated, elastic body having a first end and a second end, said body being made from a stretchable fabric having a fuzzy outer surface, said body being filled with an elastic filler;
   b. first and second attaching tapes being secured at a first end to each of said first and second ends, respectively, of said body;
   c. an expandable stitch securing at least one edge of said stretchy fabric to encase said elastic filler;
   d. hook means on a second end of said first and second attaching tapes for releasably attaching to said fuzzy outer surface near said first and second ends of said body, said attaching tapes adapted to releasably secure said endotracheal or tracheotomy tube holder via said holes in position on said patient.

7. An endotracheal or tracheotomy tube retainer for holding an endotracheal or tracheotomy tube in position on a patient comprising:
   an elongated, elastic body having a first end and a second end, said body being covered with a stretchable fabric having a fuzzy outer surface;
   first and second attaching tapes being secured at a first end to each of said first and second ends, respectively, of said elongated elastic body;
   hook means on a second end of said first and second attaching tapes for releasably attaching to said fuzzy outer surface near said first and second ends of said body; and
   tube holder means having openings in either end thereof for receiving said first and second attaching tapes therethrough, said holder having a hole in the center thereof adapted for receiving said endotracheal or tracheotomy tube therethrough.

* * * * *